(12) United States Patent
Rubinsztain et al.

(10) Patent No.: US 6,747,163 B2
(45) Date of Patent: Jun. 8, 2004

(54) METHOD FOR THE ISOLATION OF 6α, 9α-DIFLUORO-11β, 17α-DIHYDROXY-16α-METHYLPREGNA-3-OXO-1,4-DIENE-17β-CARBOXYLIC ACID

(75) Inventors: Yaacov Rubinsztain, Jerusalem (IL); Ariana Segal, Tel-Aviv (IL); Joseph Kaspi, Givatayim (IL); Ori Lerman, Givatayim (IL)

(73) Assignee: Chemagis Ltd., Tel Aviv (IL)

( * ) Notice: Subject to any disclaimer, the term of this patent is extended or adjusted under 35 U.S.C. 154(b) by 0 days.

(21) Appl. No.: 10/406,445

(22) Filed: Apr. 4, 2003

(65) Prior Publication Data

US 2004/0010155 A1 Jan. 15, 2004

(30) Foreign Application Priority Data

Jul. 9, 2002 (IL) .................................................. 150654

(51) Int. Cl.$^7$ .............................................. C07C 50/22
(52) U.S. Cl. ........................................ 552/220; 552/224
(58) Field of Search ................................. 552/220, 224

(56) References Cited

U.S. PATENT DOCUMENTS 3,636,010 A    1/1972    Anner et al.

FOREIGN PATENT DOCUMENTS

| GB | 2018256 | 10/1979 |
| WO | WO 02/08243 | 1/2002 |
| WO | WO 02051483 | * 7/2002 |
| WO | WO 02/053186 | * 7/2002 |

OTHER PUBLICATIONS

Phillipps et al., "Synthesis and Structure—Activity Relationships in a Series of Antiinflammatory Corticosteroid Analogues, Halomethyl Androstane–17β–carbothioates–17β–carboselenoates", Journal of Medicinal Chemistry, 1994, vol. 37, No. 22, pp. 3717–3729.

Kertesz et al., "Thiol Esters from Steroid 17β–Carboxylic Acids: Carboxylate Activation and Internal Participation by 17α–Acylates", J. Org. Chem. 1986, 51, pp. 2315–2328.

* cited by examiner

*Primary Examiner*—Paul J. Killos
(74) *Attorney, Agent, or Firm*—Banner & Witcoff, Ltd.

(57) ABSTRACT

The invention provides a process for the preparation and isolation of compound of formula 2, comprising the following steps:

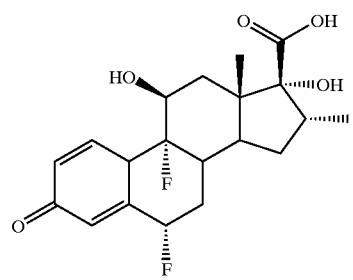

oxidizing Flumethasone dissolved in a tetrahydrofuran–water mixture with periodic acid at a temperature lower than 30° C.; cooling the reaction mixture to a temperature lower than 10° C.; adding an antisolvent precooled to a temperature lower than 10° C.; and separating the precipitated crystal by filtration, whereby there is obtained a compound of formula 2 in a yield of at least 98% and of a chromatographic purity of at least 99%.

4 Claims, No Drawings

METHOD FOR THE ISOLATION OF 6α, 9α-DIFLUORO-11β, 17α-DIHYDROXY-16α-METHYLPREGNA-3-OXO-1,4-DIENE-17β-CARBOXYLIC ACID

The present invention relates to a method for the isolation of 6α,9α-Difluoro-11β, 17α-Dihydroxy-16α-Methylpregna-3-Oxo-1,4-Diene-17β-Carboxylic Acid.

6α,9α-difluoro-11β, 17α-dihydroxy-16α-methylpregna-3-oxo-1,4-diene-17β-carboxylic acid (2) is a key intermediate in the preparation of Fluticasone propionate (3), a well known antiallergic and anti-inflammatory corticosteroid that is a very efficient drug for the treatment of asthma and chronic pulmonary diseases. 2 is usually obtained by the oxidation of flumethasome (1) using conventional oxidation reagents as described in equation 1.

Equation 1

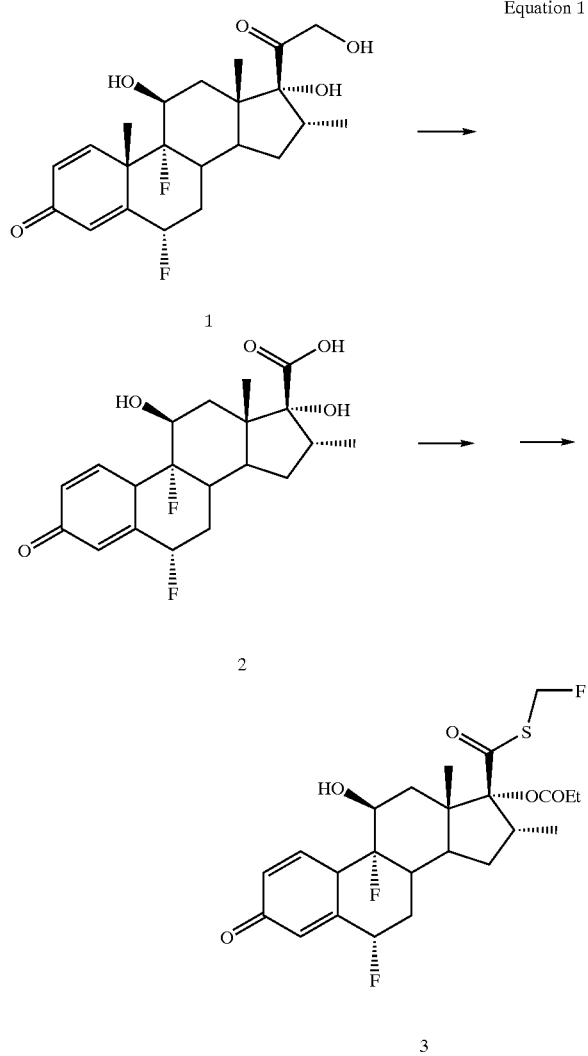

The oxidation of 1 to 2 was described in U.S. Pat. No. 3,636,010 (1969). 1 is oxidized to 2 using periodic acid. The reaction is carried out in dioxane as solvent at ambient temperature. Water is added, part of the dioxane is evaporated and the compound 2 formed is filtered.

In J. Med. Chem. 37 (1994) 3721, the authors describe a similar process in which flumethasone is dissolved in tetrahydrofuran (THF). It is then oxidized using an aqueous solution of periodic acid. The THF is then evaporated and the solid is filtered. No temperature data are given.

In J. Org. Chem 51 (1986) 2315, flumethasone is oxidized at 20° C. with periodic acid in methanolic medium. The volume of the solvent is reduced and ice water is added. The precipitation formed is filtered.

A different oxidation method of flumethasone to compound 2 is described in patent GB 2018256. Flumethasone is dissolved in methanol in the presence of potassium carbonate while a stream of air is bubbled through the solution at ambient temperature. Water is added, the pH is brought to 2. Most of the methanol is evaporated and the resulting crystalline precipitation is collected by filtration.

A recent patent application, WO 0208243, claims the separation method of compound 2 after the oxidation process.

The oxidation is carried out with periodic acid in THF water mixture. The inventors proclaim that it is advisable to add an antisolvent in order to precipitate the carboxylic acid formed. To their surprise, they discovered that controlling the conditions under which the antisolvent is added is essential.

Particularly, they comment that if water at 0–5° C. is added as antisolvent, the crystalline product produced is very voluminous, it resembles a soft gel and it is very difficult to filter. When water is added around ambient temperature, a sand-like consistency that is very easily filtered is produced.

Officially, they claim in this patent that the addition of the antisolvent is carried out at a temperature higher than 10° C., preferably around 22° C.

Surprisingly, it has now been found that quality, the yield, the crystalline form and the efficiency of the filtration are uniform also if the antisolvent is added at a temperature lower than 10° C. and that contrary to the teachings of WO 02/08243 there is no difference in the quality yield, crystalline form and the efficiency of the filtration between carrying out the process at a temperature above 10° C. and a temperature below 10° C. e.g., a temperature between the range of −2° C. and 10° C. In fact it has now been found that a very pure product, i.e., one having a chromatographic purity of at least 99% is obtained in yields of at least 98% when the precipitation is carried out at temperatures lower than 10° C.

Thus the present invention relates to the isolation of 6α,9α-difluoro-11β,17α dihydroxy-16α-methylpregna-3-oxo-1,4-diene-17β-carboxylic acid (formula 1) obtained as the result of the oxidation of flumethasone with periodic acid in THF-water medium.

More specifically the present invention provides a process for the preparation and isolation of compound of formula 2, comprising the following steps:

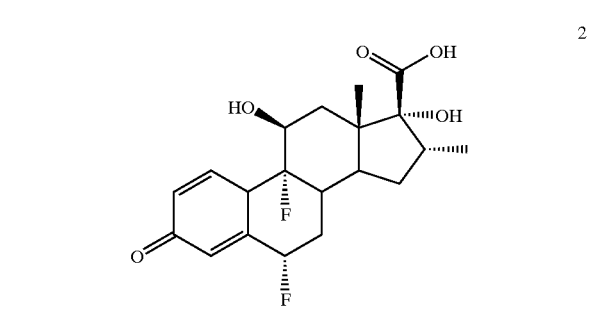

i. oxidizing Flumethasone dissolved in a tetrahydrofuran-water mixture with periodic acid at a temperature lower than 30° C.

ii. cooling the reaction mixture to a temperature lower than 10° C.;

iii. adding an antisolvent precooled to a temperature lower than 10° C.; and iv. separating the precipitated crystal by filtration, whereby there is obtained a compound of formula 2 in a yield of at least 98% and of a chromatographic purity of at least 99%.

Though, compound 2 can be produced by the oxidation of flumethasone with periodic acid in THF/water medium, the product formed can be very easily separated by filtration after the addition of water at a wide range of temperatures. However, at temperatures lower than 0° C., precipitation becomes voluminous and is rather difficult to be separated by filtration.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

In a 1L three neck flask 60 gr of Flumethasone (0.146 mole, 1 eq.) is dissolved in 270 ml THF and 50 ml $H_2O$ to give a clear solution. A solution of 51 gr $H_5IO_6$ (0.223, mole, 1.5 eq.) in 100 ml $H_2O$ (distilled) is added dropwise to the solution during 1.5–2 hours. The reaction is exothermic and should be kept below 30° C. by cooling with a water bath.

At the end of the addition, the mixture is stirred for another 10 min, then monitored by HPLC to confirm end of reaction. The reaction mixture is cooled to 2–4° C. and a mixture of 600 gr ice water (2–4° C.) is added, keeping the reaction mixture below 5° C.

The stirring is continued for an additional 15 minutes (below 5° C.) and the precipitated 17-β-carboxylic acid is filtered and washed five times with 50 ml cold water (2–4° C.) (pH of the last washing: 5–6). The crystals obtained are large and no filtration problems were observed. The product is dried in an air circulation oven at 60° C. overnight.

Dried weight: 57.5 gr. Yield: 99.0%. Purity: 99.6%.

EXAMPLES 2–4

By the same way a series of experiments were performed and the results are shown in the following table:

| Example | Flumethasone (gr) | Work-up Temp. (° C.) | Filtration | Dry 17β- (gr) | Yield (%) | Purity (%) |
|---|---|---|---|---|---|---|
| Example 2 | 15 | 40–45 | Fast | 13.5 | 93.1 | 99.7 |
| Example 3 | 15 | −2 | Fair | 14.2 | 98.0 | 99.7 |
| Example 4 | 15 | 22 | Fast | 14.0 | 96.5 | 99.7 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the preparation and isolation of compound of formula 2, comprising the following steps:

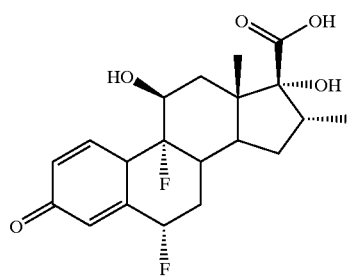

a. oxidizing Flumethasone dissolved in a tetrahydrofuran-water mixture with periodic acid at a temperature lower than 30° C.;

b. cooling the reaction mixture to a temperature lower than 10° C.;

c. adding an antisolvent precooled to a temperature lower than 10° C.; and d. separating the precipitated crystal by filtration, whereby there is obtained a compound of formula 2 in a yield of at least 98% and of a chromatographic purity of at least 99%.

2. A process according to claim 1 wherein the antisolvent is water.

3. A process according to claim 1 wherein the reaction mixture is cooled to a temperature range between 0–5° C.

4. A process according to claim 1 wherein the antisolvent is precooled to a temperature range between 0–5° C.

* * * * *